(12) United States Patent
Shima (10) Patent No.: US 6,210,160 B1
(45) Date of Patent: Apr. 3, 2001

(54) COVER FOR WORKING CAST AND ARTICULATOR

(75) Inventor: Fumio Shima, Tokushima (JP)

(73) Assignee: Shiken Corporation, Tokushima (JP)

( * ) Notice: Subject to any disclaimer, the term of this patent is extended or adjusted under 35 U.S.C. 154(b) by 0 days.

(21) Appl. No.: 09/282,208

(22) Filed: Mar. 31, 1999

(30) Foreign Application Priority Data

Nov. 12, 1998 (JP) .................................................. 10-322495

(51) Int. Cl.[7] .................................................. A61C 11/00
(52) U.S. Cl. .................................................. 433/60
(58) Field of Search .................................. 433/60, 34, 45, 433/47

(56) References Cited

U.S. PATENT DOCUMENTS

| | | | |
|---|---|---|---|
| 5,076,786 | * 12/1991 | Callne | 433/60 |
| 5,622,497 | * 4/1997 | Cho | 433/60 |
| 5,730,593 | * 3/1998 | Mack | 433/60 |
| 5,749,725 | * 5/1998 | Chinlund | 433/60 |

\* cited by examiner

Primary Examiner—Nicholas D. Lucchesi
(74) Attorney, Agent, or Firm—Wenderoth, Lind & Ponack, L. L. P.

(57) ABSTRACT

A cover for a working cast makes it extremely easy to mount and dismount a working cast to and from an articulator, improves workability, and keeps the working cast as pollution-free as possible. An articulator is also proposed. The articulator has a base and a support member each carrying a rotatable and pivotable retainer plate. Each retainer plate can be fixed in position by turning a knob. Each retainer plate has a magnet plate on its outer surface. On the other hand, a base portion of a master model having a tooth portion is kept covered with the cover when molded. The cover has on its bottom surface a magnet plate. By magnetic attraction between the magnet plates of the cover and one of the retainer, the master model can be mounted on the articulator. On the other hand, a tooth portion of an antagonist model is fixed to a base member. The antagonist model is mounted on the articulator by magnetic attraction between a magnet plate provided on the bottom of the base plate and the magnet plate on one of the retainer plates.

31 Claims, 10 Drawing Sheets

COVER FOR WORKING CAST AND ARTICULATOR

BACKGROUND OF THE INVENTION

This invention relates to a working cast which can be easily attached to and detached from an articulator, a cover for a working cast which also serves as a mold, and an articulator to which the working cast can be mounted.

To manufacture a crown restoration, a working cast is manufactured first. Then a master model and an antagonist model are mounted on an articulator to adjust the occlusion between the master model and the antagonist model.

Figure 20:
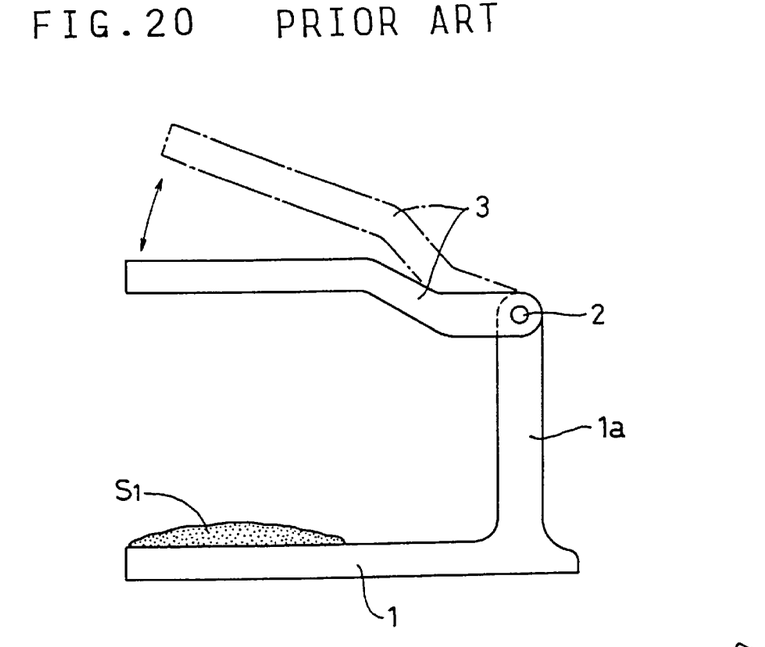
FIG. 20 is a side view of a conventional articulator.
Figure 21:
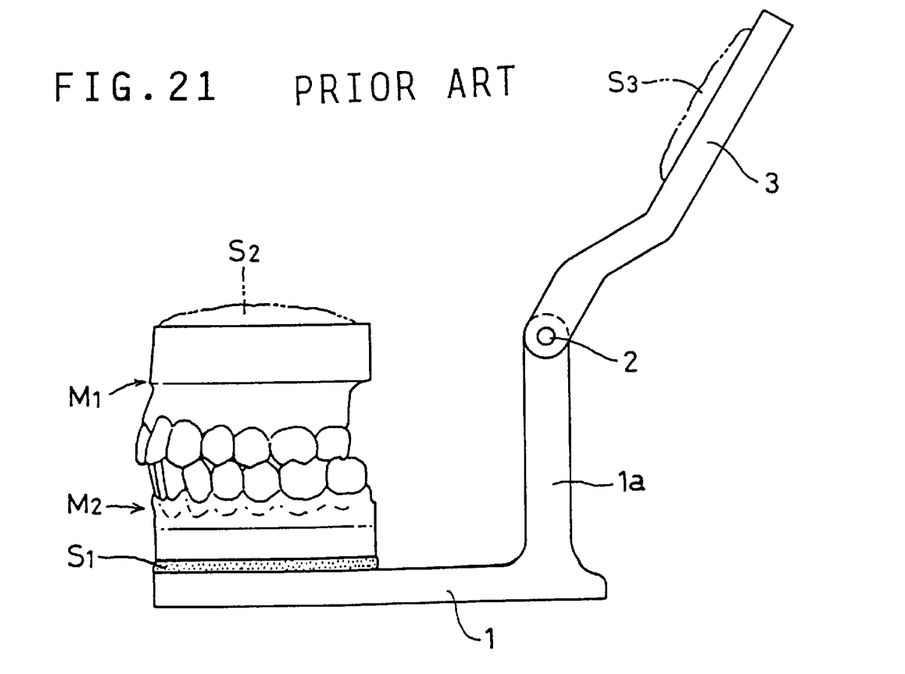
FIG. 21 is a side view showing how it is used.

As shown schematically in FIG. 20, such an articulator comprises a base 1 having a column 1a, and a support arm 3 pivotally mounted to the top of the column 1a by a pin 2. To mount a working cast, as shown in FIG. 21, plaster paste S1 is heaped on the base 1, and plaster paste S2 is also heaped on the top of a master model M1 whose bite with respect to an antagonist model M2 has been fixed by wax beforehand, and further a small amount of plaster paste S3 is optionally applied to the bottom of the support arm 3. Then, the models M1 and M2 are placed together on the paste S1, the support arm 3 is pivoted onto the master model M1, and positions of the models M1, M2 are adjusted in this state. Any excess plaster paste protruding from the outer periphery is removed by fingers or a knife.

It is thus extremely troublesome to mount a working cast on an articulator. It is also very time-consuming and low in efficiency to remove the model after the plaster has hardened. It is also necessary to remove plaster stuck on the bottom of the model.

An environment where crown restorations are manufactured is usually scattered with dust including plaster powder, metallic and ceramic powder and wax chips and thus extremely messy. Such dust tends to adhere to the models, thus necessitating cleaning of the models.

An object of this invention is to simplify the attaching and detaching of a working cast to and from an articulator, thereby markedly improving work efficiency.

Another object of this invention is to keep working casts as dust-free as possible.

SUMMARY OF THE INVENTION

According to this invention, there is provided a cover for a working cast which also serves as a mold, the cover comprising an outer surface protective member having a substantially semioval bottom wall, an end wall and a peripheral wall, a gripper having a pair of gripper plates and having an open end, and an engaging means for engagement with an articulator, the gripper being detachably mounted in the outer surface protective member such that the open end faces toward a tip of the outer surface protective member.

The engaging means may be a magnetic member. Also, the outer surface protective member should be formed with a through hole so that the gripper can be pushed out of the protective member by pushing through the hole. The gripper should have a partitioning plate extending to the tip of the outer surface protective member to form a cover for a one-side jaw model.

A positioning means should preferebly be provided on the bottom wall of the outer surface protective member for positioning of the cover on the articulator.

For an antagonist model, a base member having an engaging means and a positioning means is provided. The master model with the cover and the antagonist model with the base member are mounted on the articulator which has retaining plates for retaining the cover and the base member. The retaining plates each have a magnetic member which attracts a magnetic member of the cover and the base member. The retaining plates also have positioning means for positioning the cover and the base member with respect to the articulator.

Other features and objects of the present invention will become apparent from the following description made with reference to the accompanying drawings, in which:

BRIEF DESCRIPTION OF THE DRAWINGS

FIG. 9 is a vertical sectional view of an article molded using a cover for a;

DETAILED DESCRIPTION OF THE PREFERRED EMBODIMENT

Figure 1:
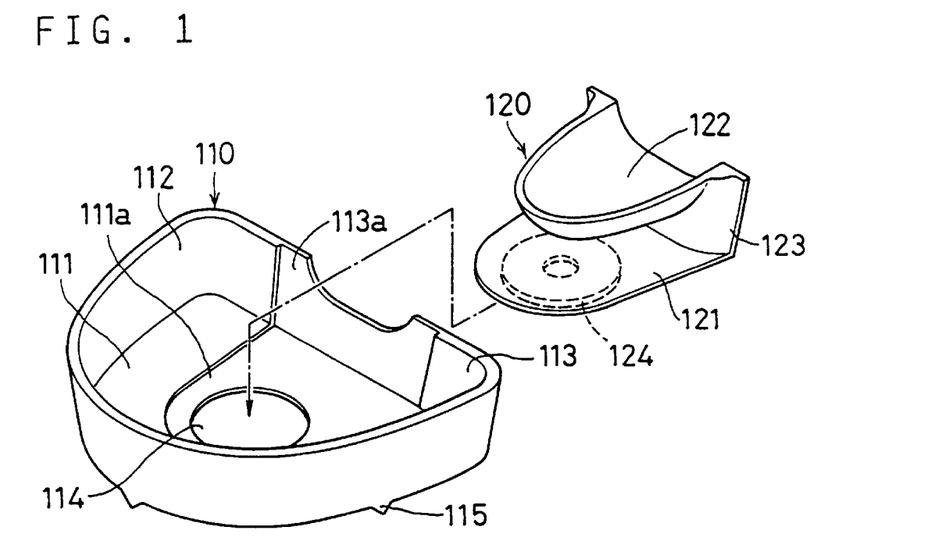
FIG. 1 is an exploded perspective view of a full jaw cover according to this invention.
Figure 2:
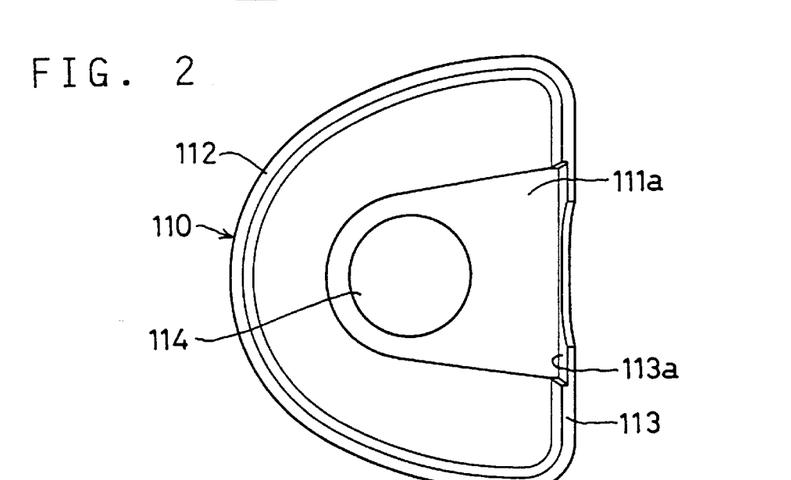
FIG. 2 is a plan view of an outer surface protective member of the cover.

An embodiment of this invention is now described with reference to FIGS. 1–19. FIGS. 1 through 5 show a cover for protecting a base of a full jaw model. This cover also serves as a mold. As shown in FIGS. 1 and 2, a cover 100 for a full jaw model has an outer surface protective member 110, and a gripper 120 for gripping the bottom of the base. The outer surface protective member 110 comprises a bottom wall 111 having a substantially semioval shape, and a peripheral wall 112 and an end wall 113 provided along the edge of the bottom wall 111 so as to completely surround the wall 111. The peripheral wall 112 and the end wall 113 are of a substantially uniform height over the entire circumference, but are preferably tapered slightly outwardly. Formed in the middle of the end wall 113 is a vertical recess 113a for receiving an end plate of the gripper 120. Contiguous with the recess 113a, the bottom wall 111 is formed with a tapered recess 111a with a round tip and a through hole 114 near the tip (FIG. 2).

Figure 3:
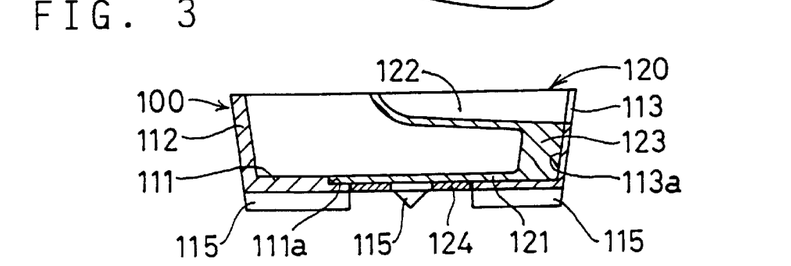
FIG. 3 is a vertical sectional view of the cover.
Figure 4:
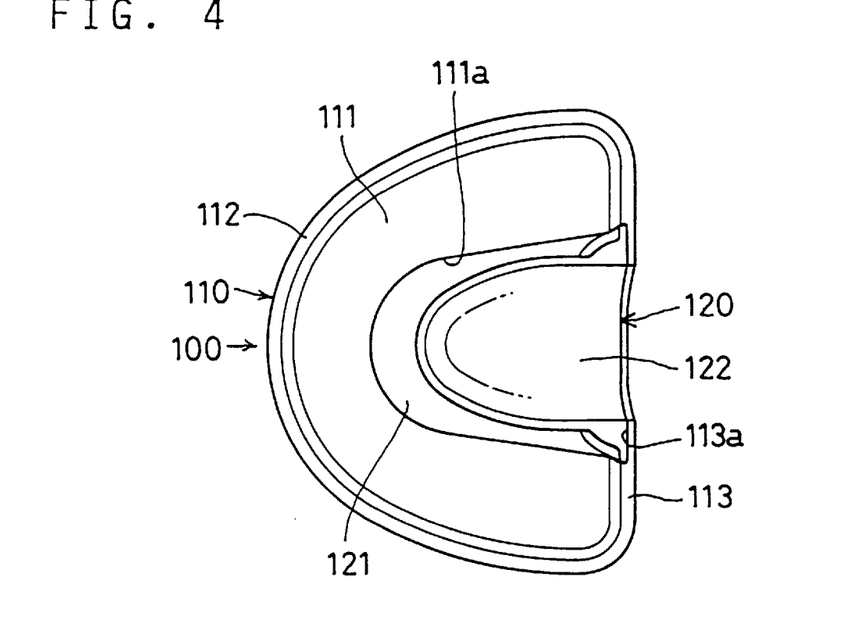
FIG. 4 is a plan view of the cover.

As shown in FIGS. 1 and 3, the gripper 120 comprises a lower gripper plate 121 complementary in shape and height to the recess 111a of the bottom plate 111 of the protective member 110, a tongue-shaped upper gripper plate 122, and an end plate 123 connecting the upper and lower plates 121, 122 together. The lower gripper plate 121 carries on its bottom a magnet plate 124 adapted to fit in the through hole 114. As seen in FIGS. 3 and 4, the gripper 120 can fit snugly in the recesses 111a and 113a of the outer surface protective member 110 so that the tops of the bottom wall 111 and the lower gripper plate 121 are flush with each other.

Figure 5:
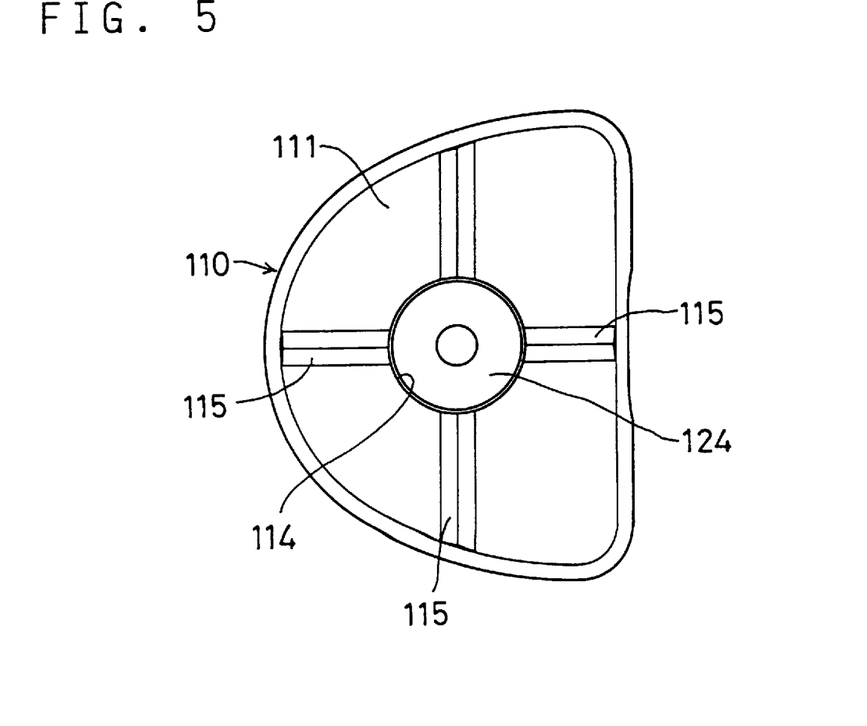
FIG. 5 is a bottom view of the cover.
Figure 6A:
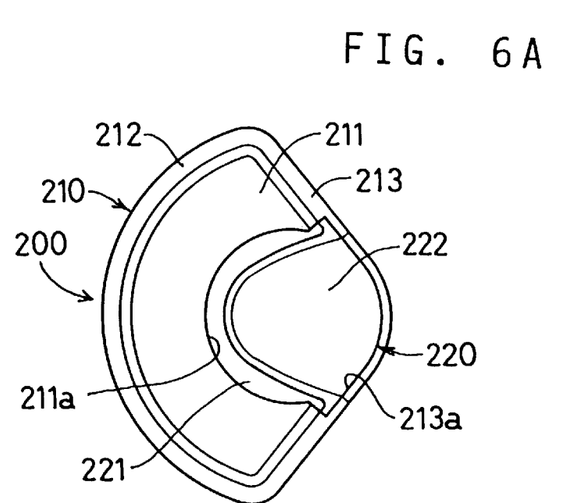
FIG. 6A is a plan view of a cover for an anterior tooth portion.
Figure 6B:
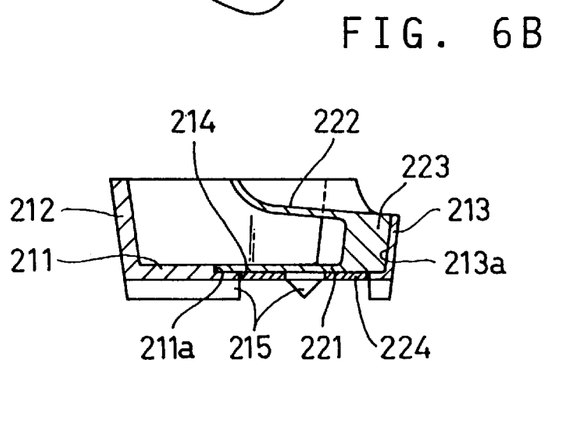
FIG. 6B is a vertical sectional view of the same.
Figure 7A:
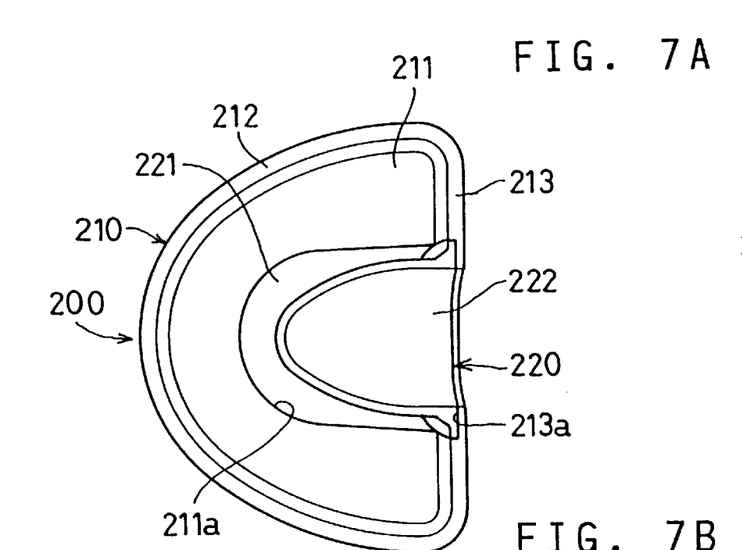
FIG. 7A is a plan view of another cover for an anterior tooth portion.
Figure 7B:
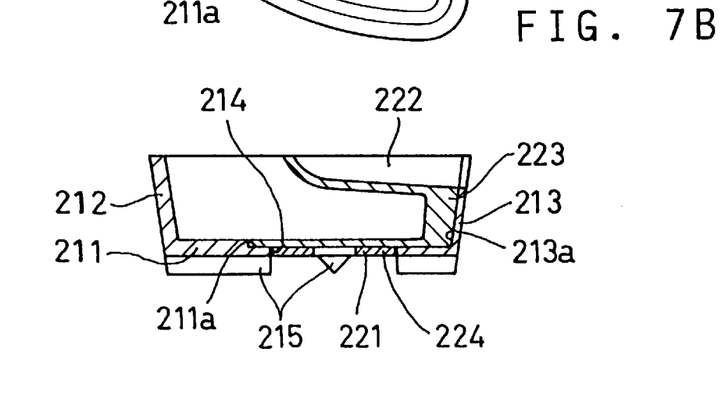
FIG. 7B is a vertical sectional view of the same.

Referring to FIGS. 3 and 5, ribs 115 having a triangular section are formed on the back of the outer surface protective member 110 along centerlines crossing each other at an angle of 90°. The functions of the ribs are described below. The upper gripper plate 122 is recessed like a tray so that it fits in the base of the full jaw model.

FIGS. 6A–7B show a mold/cover used for the manufacture of an anterior tooth model. Structurally, FIGS. 6A–7B are the same as the cover 100 for full jaw model except the range of its anterior tooth portion. In the figures, a mold/cover 200 has an outer surface protective member 210, a bottom wall 211, a semioval recess 211a, a peripheral wall 212, an end wall 213, a vertical recess a through hole 214, ribs 215, a gripper 220, a lower gripper plate 221, an upper gripper plate 222, an end plate 223, and a magnet plate 224.

Figure 8A:
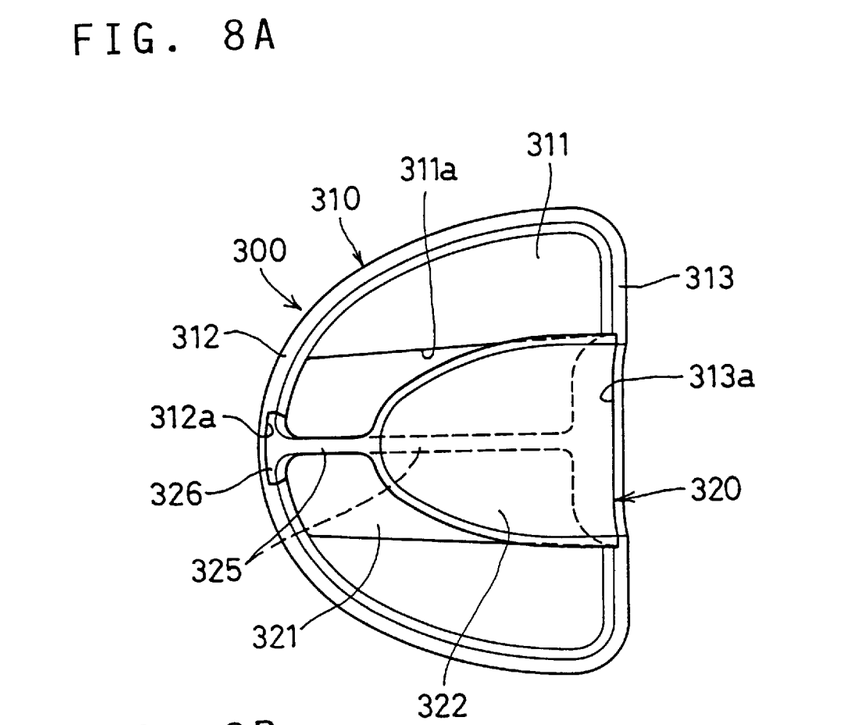
FIG. 8A is a plan view of a cover for one-side jaw model.
Figure 8B:
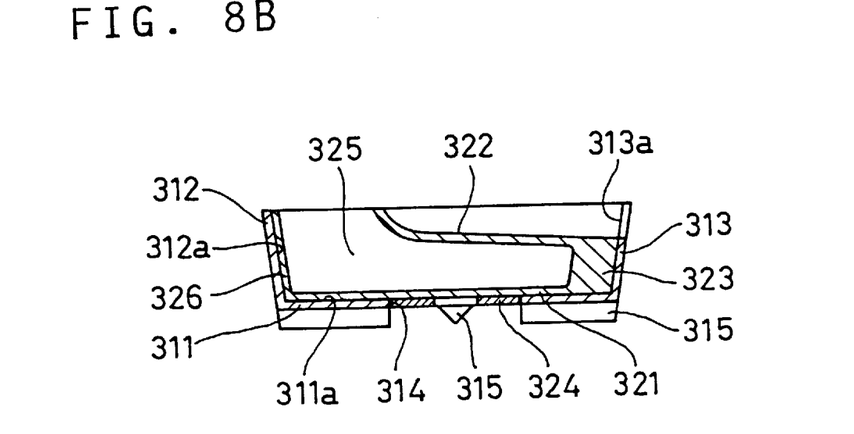
FIG. 8B is a vertical sectional view of the same.

FIGS. 8A and 8B show a mold/cover 300 for use in the manufacture of a one-side jaw model. As shown, the cover 300 comprises an outer surface protective member 310 and a gripper 320. The former comprises a substantially semioval bottom wall 311, and a peripheral wall 312 and an end plate 313 surrounding the bottom wall 311, and is shaped like a container. The end plate 313 has a vertical recess 313a. Contiguous with the recess 313a, the bottom wall 311 is formed with a tapered recess 311a having its tip extending to a vertical recess 312a formed in the inner surface of the peripheral wall 312 at its tip.

The gripper 320 comprises a lower gripper plate 321 adapted to fit in the tapered recess 311a, and a tongue-shaped upper gripper plate 322. The gripper plates 321 and 322 are connected together by an end plate 323 and a partitioning plate 325. The plate 325 extends along the center line of the gripper plates 321, 322, and has at its tip an engaging piece 326 received in the vertical recess 312a of the peripheral wall 312. The protective member 310 further has a through hole 314 formed in the bottom wall 311 and ribs 315 provided on the bottom of the bottom wall 311. A magnet plate 324 is secured to the bottom of the lower gripper plate 321.

Figure 9:
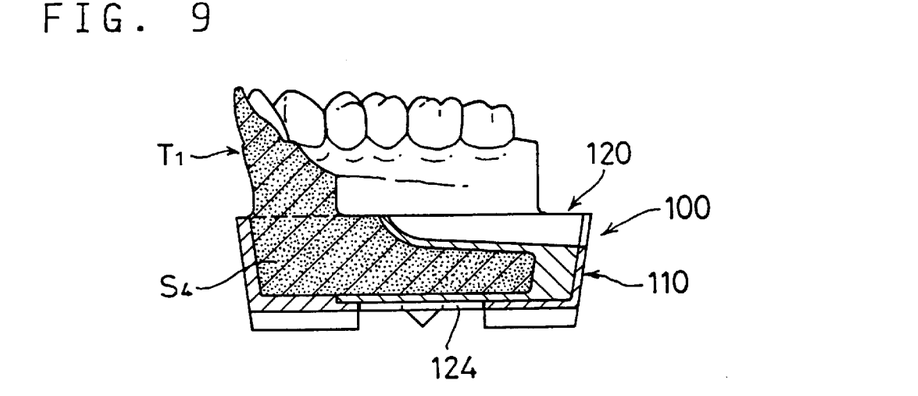
Figures 10, 11:
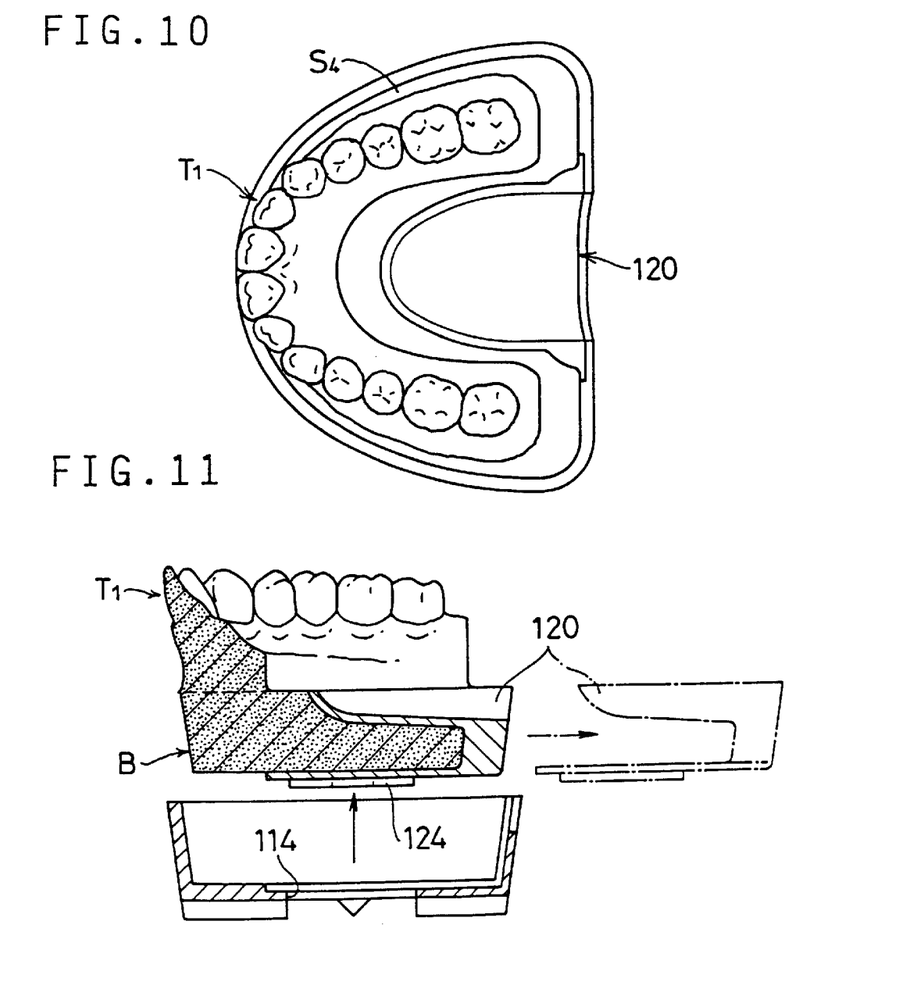
FIG. 10 is a plan view of the same.
FIG. 11 is a vertical sectional view showing how the model is taken out of the cover.

Description is now made of how a working cast is manufactured using the cover 100. As shown in FIGS. 9 and 10, a release agent is applied to the inner surface of the cover 100 in the state of FIG. 3, and plaster paste S4 is poured into the cover 100. A tooth portion T1 formed beforehand is then pressed so that its bottom becomes flush with the edge of the cover 100. Of course, dowel pins provided in the tooth portion T1 beforehand are buried completely in the plaster paste S4 in the cover 100. Any excess paste S4 is removed by a finger or a knife and the paste is allowed to harden.

When the paste hardens, the assembly is handled without removing the cover 100. But if desired, the molded base portion B is removable from the outer surface protective member 110 together with the gripper 120 by pushing the magnet plate 124 upward as shown in FIG. 11. The gripper 120 is also removable by pulling it rightwardly in FIG. 11 as shown by an arrow.

The cover 200 for an anterior tooth model and the cover 300 for a one-side jaw model are also used in the same manner, except that in the case of the cover 300, plaster paste is poured into only one of two spaces defined on opposing sides of the partitioning plate 325.

Figure 12:
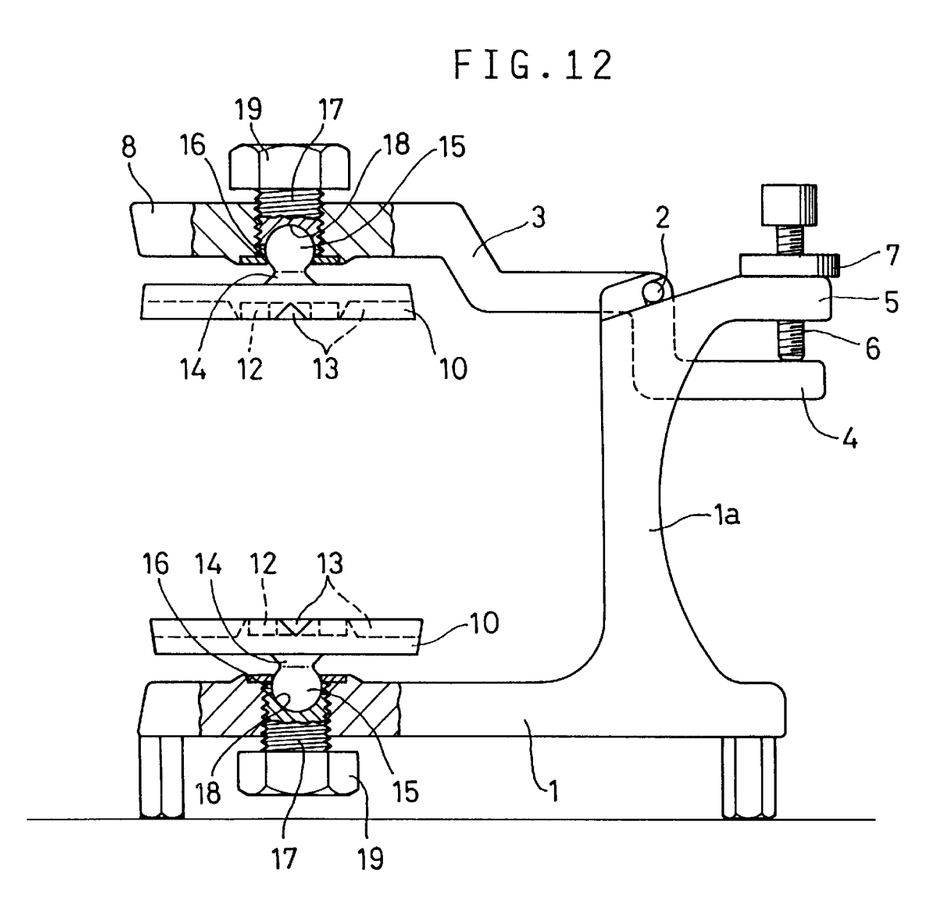
FIG. 12 is a partially cutaway side view of an articulator.
Figure 13:
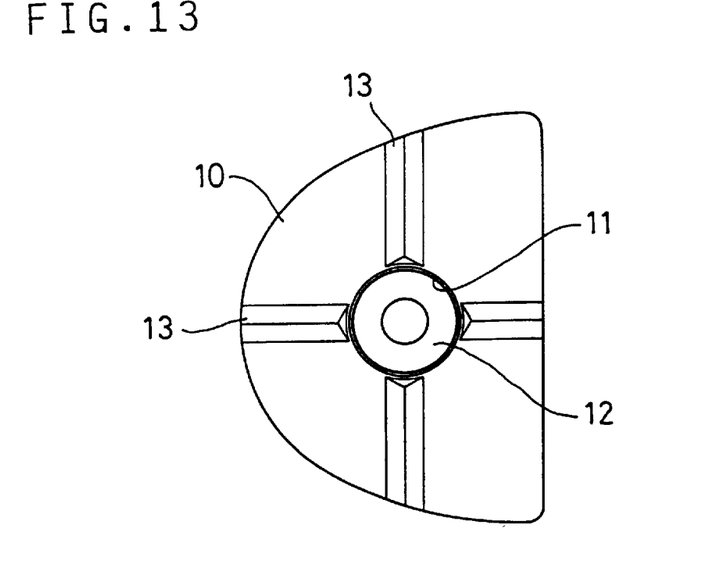
FIG. 13 is a plan view of a retainer plate of the articulator.

An articulator on which the thus molded working cast is to be mounted is now described with reference to FIGS. 12 and 13. As shown in FIG. 12, a support column 1a extends substantially perpendicularly from one end of a base 1. A support arm 3 is pivotally mounted to the top end of the support column 1a by a pin 2. The support arm 3 has an integral stop piece 4 extending in the opposite direction to the arm 3. A support piece 5 extends from the top end of the support column 1a in the same direction in which the stop piece 4 extends. A threaded pin 6 is threaded into the support piece 5 with its tip in abutment with the stop piece 4, thus limiting the pivoting motion of the support arm 3. Thus, by turning the threaded pin 6, it is possible to pivot the support arm 3 toward and away from the base 1. The threaded pin 6 is held in position by a nut 7 threaded onto the pin 6.

Retainer plates 10 are mounted to the bottom of a support member 8 provided at the tip of the support arm 3 and to the top surface of the base 1. As shown in FIGS. 12 and 13, the retainer plates 10 are semioval members having a flat top and a flat bottom respectively formed with a recess 11 in the center. A magnet plate 12 is secured in each recess 11. Each retainer plate 10 has four retaining grooves 13 having a triangular section and extending radially from the recess 11 and spaced at equal angular intervals of 90°. The grooves 13 extend to the edges of the retainer plates 10. They are complementary in shape and position to the ribs 115, 215 and 315 formed on the bottoms of the covers 100, 200 and 300.

Each retainer plate 10 carries on its back a stem 14 extending from the center of the plate 10 and having a ball 15 at the tip. The ball 15 is received loosely in a socket 16 formed in the base 1 and the support member 8 so as not to come out of the socket. The retainer plates 10 are thus rotatable and pivotable relative to the base 1 and the support member 8. Each socket 16 is a threaded hole into which is threaded a bolt 17. The bolt 17 has at its tip a spherical recess 18. By turning the bolt head 19 in one direction, the ball 15 is pushed by the bolt 17 and pressed against the edge of the bottlenecked opening of the socket 16 to keep the ball unmovable. In this state, the support plate 10 can neither rotate nor pivot, but is fixed in position. By turning the bolt head 19 in the opposite direction, the ball 15 can be moved away from the socket edge, so that the plate 10 is now rotatable and pivotable.

Figure 14:
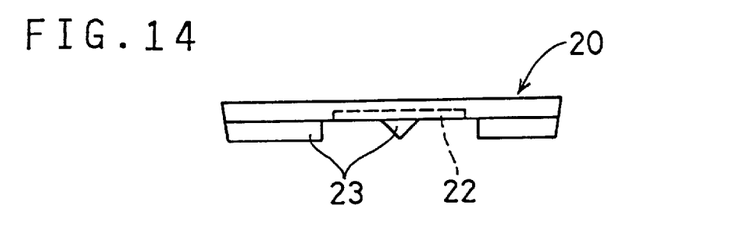
FIG. 14 is a side view of a base member of an antagonist model.
Figure 15:
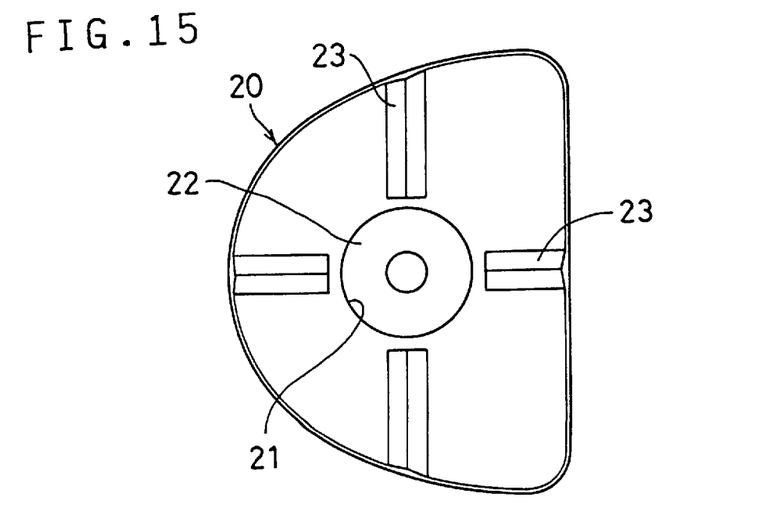
FIG. 15 is a back view of the same.

A base member 20 for mounting an antagonist model on the articulator is now described. As shown in FIGS. 14 and 15, the base member 20 is a substantially semioval, flat plate having a recess 21 in the center of the back. A magnet plate 22 is secured in the recess 21. Four ribs 23 extend radially from the recess 21, spaced at angular intervals of 90°. These ribs 23 are complementary in shape and position to the retaining grooves 13 of the retainer plates 10 of the articulator.

To the surface of the base member 20, a tooth portion of an antagonist model is secured by means of an adhesive in general and an instantaneous adhesive in particular, or by applying an adhesive beforehand.

Figure 16:
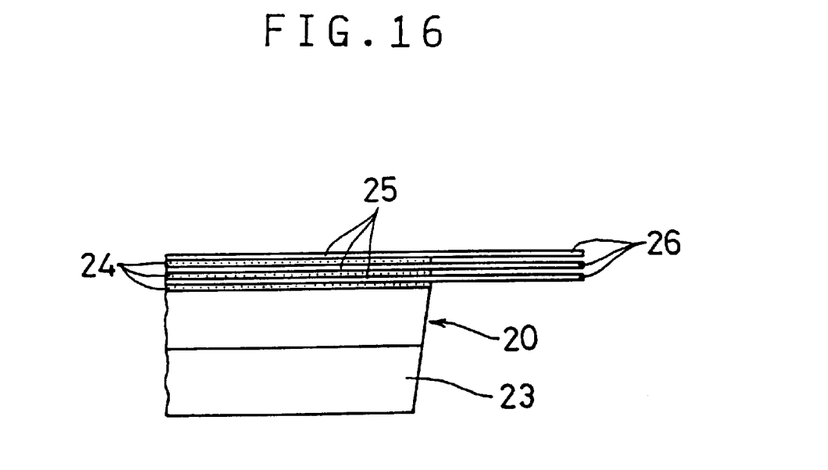
FIG. 16 is a partial enlarged vertical sectional view of a different base member.

As shown in FIG. 16, a plurality of adhesive layers 24 and release paper sheets 25 may be alternately laminated. By peeling the outermost release paper sheet before bonding each antagonist model, this laminate can be used a plurality of times. Numeral 26 designates tabs of the release paper sheets 25.

Figure 17:
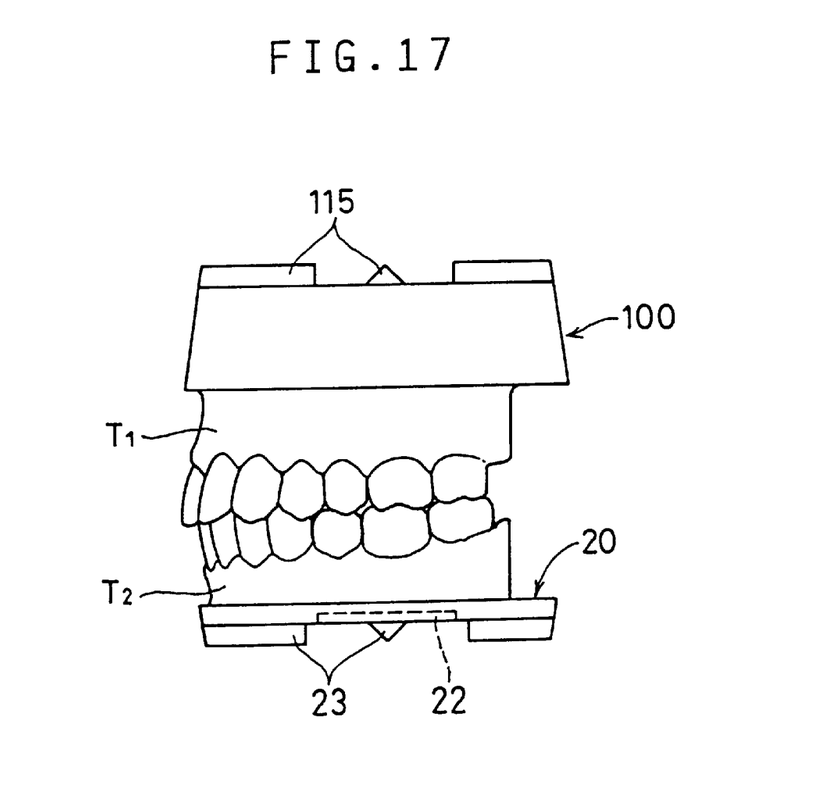
FIG. 17 is a side view of the cover in use.
Figure 18:
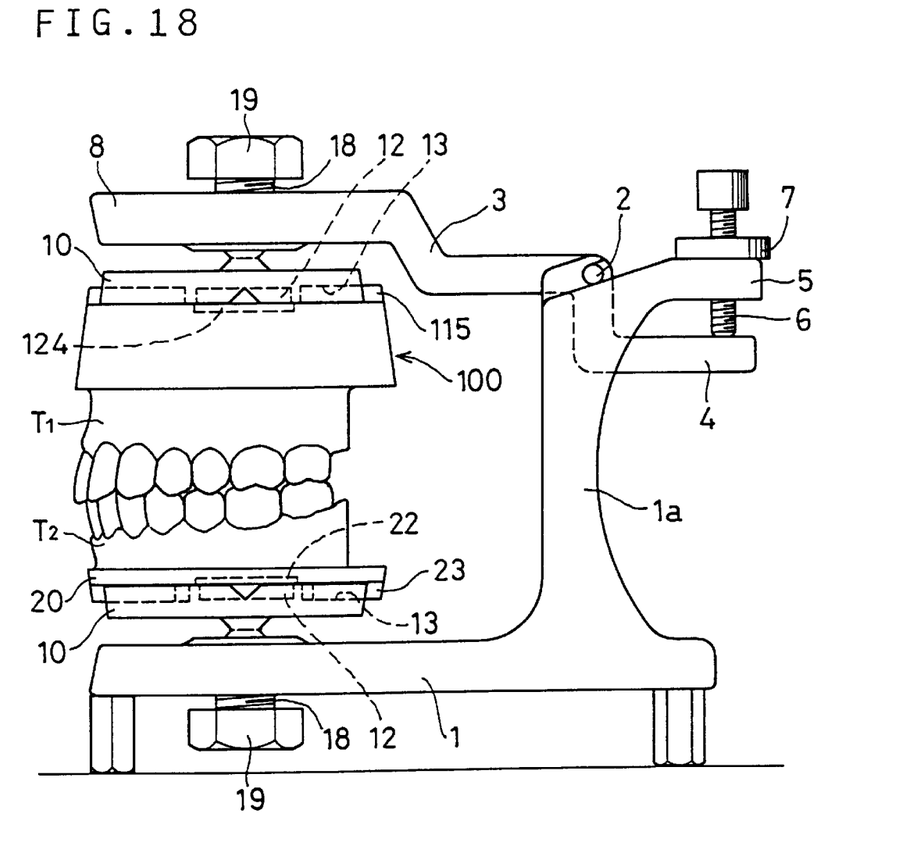
FIG. 18 is a side view showing the model mounted on the articulator together with the cover.

The master model and the antagonist model may be mounted on the articulator e.g. in the following manner. Of course, the order of mounting steps is not limited to that shown. First, as shown in FIG. 17 the, bite of the tooth portion T2 of the antagonist model with respect to the master model formed in FIG. 9 with the cover 100 on the master model is fixed with wax. The base member 20 of FIGS. 14, 15 is fixed to the underside of the tooth portion T2. Then, as shown in FIG. 18, the magnet plate 124 provided on the back of the cover 100 is attracted to the magnet plate 12 provided on the retainer plate 10 of the articulator.

At this time, the retainer plate 10 and the cover 100 are positioned relative to each other by the engagement of the ribs 15 of the cover 100 in the grooves 13 of the retainer plate 10. The upper and lower retainer plates 10 are not fixed but kept rotatable and pivotable. In this state, the magnet plate 12 of the retainer plate 10 on the base 1 is attracted to the magnet plate 22 provided on the base member 20 of the antagonist model with the ribs 23 engaged in the retaining grooves 13. The base member 20 is thus fixed in position relative to the retainer plate 10. The models are then moved (this is possible because the upper and lower retainer plates 10 are still rotatable and pivotable) so that the tooth portions T1 and T2 of the master model and the antagonist model are substantially parallel to the base 1 and the support member 8, respectively. They are then fixed in position by turning the upper and lower bolt heads 19.

The base member 20 may be firstly fixed to the retainer plate 10 on the base 1 without fixing the base member 20 to the tooth portion T2 of the antagonist model beforehand. Also, adjustment may be made after the master model and the antagonist model have been mounted on the upper and lower retainer plates 10 without fixing the bite between the master model and the antagonist model beforehand.

The anterior tooth model with the cover 200 and the one-side jaw model with the cover 300 are also mounted in the same manner. The order of mounting steps is not limited.

Figure 19:
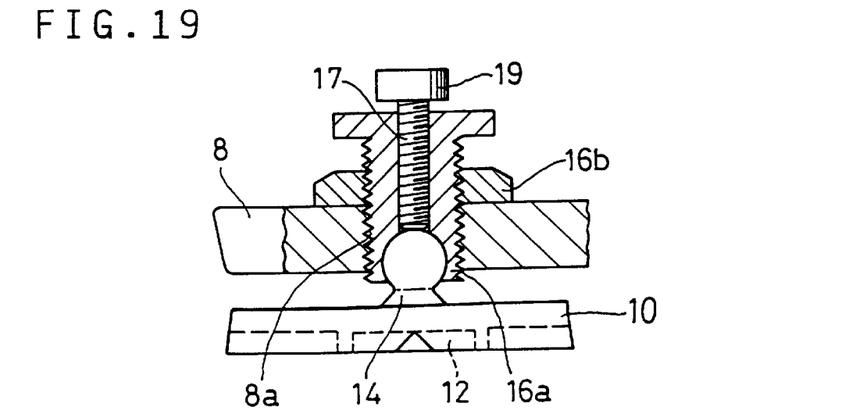
FIG. 19 is a partial enlarged vertical sectional view of a different articulator.

FIG. 19 shows an embodiment in which the socket for rotatably and pivotably retaining the stem 14 of each retainer plate 10 is vertically movable. A socket member 16a is threaded into a threaded hole 8a formed in the support member 8 (or a base 1) so as to be vertically movable. The socket member 16 is fixed in position by a nut 16b.

In the above embodiment, as means for detachably mounting the cover 100 and the base member on the articulator, magnet plates are attracted to each other. Of course, one of the magnets may be replaced with a ferromagnetic member. Further, the mounting means may be a press-fit member such as a snap button or an adhesive. Such means may be provided on either of the gripper and the outer surface protective member. As positioning means, ribs and grooves are used in the embodiment, but any other combination of male and female elements may be used.

According to this invention, as described above, it is possible to mold a base portion of a working cast using a cover having also the function as a mold and to handle the working cast without removing the cover. Thus, it is possible to form a working cast and also protect it using a single cover. The working cast can thus be kept clean and undamaged. Since there is no need to use plaster to mount the working cast on the articulator, to remove plaster thereafter, and to clean the articulator and the model, workability improves dramatically, and the amount of plaster needed decreases, which leads to a cost reduction. Work environments also improve because no plaster powder flies up in the air during cleaning.

Also, dowel pins of the tooth portion of the working cast will not be pushed up by plaster when the working cast is mounted on the articulator.

What is claimed is:

1. A cover for a working cast which also serves as a mold, said cover comprising an outer surface protective member having a substantially semioval bottom wall, an end wall and a peripheral wall, a gripper having a pair of gripper plates and having an open end, and an engaging part for engagement with an articulator, said gripper being detachably mounted in said outer surface protective member such that said open end faces toward a tip of said outer surface protective member.

2. The cover as claimed in claim 1 wherein said engaging part comprises a magnetic member.

3. The cover as claimed in claim 2 wherein said outer surface protective member has a through hole so that said gripper mounted in said outer surface protective member can be pushed out of said protective member by pushing through said hole.

4. The cover as claimed in claim 2 wherein said gripper has a partitioning plate extending along a central axis of said gripper toward the tip of said outer surface protective member.

5. The cover as claimed in claim 2 further comprising a positioning part provided on an outer surface of the bottom wall of said outer surface protective member for holding the cover in position when engaged with an articulator.

6. The cover as claimed in claim 1 wherein said outer surface protective member has a through hole so that said gripper mounted in said outer surface protective member can be pushed out of said protective member by pushing through said hole.

7. The cover as claimed in claim 6 wherein said gripper has a partitioning plate extending along a central axis of said gripper toward the tip of said outer surface protective member.

8. The cover as claimed in claim 6 further comprising a positioning part provided on an outer surface of the bottom wall of said outer surface protective member for holding the cover in position when engaged with an articulator.

9. The cover as claimed in claim 1 wherein said gripper has a partitioning plate extending along a central axis of said gripper toward the tip of said outer surface protective member.

10. The cover as claimed in claim 9 further comprising a positioning part provided on an outer surface of the bottom wall of said outer surface protective member for holding the cover in position when engaged with an articulator.

11. The cover as claimed in claim 1 further comprising a positioning part provided on the outer surface of the bottom wall of said outer surface protective member for holding the cover in position when engaged with an articulator.

12. A working cast arrangement comprising: a working cast including a tooth portion and a base portion; and a cover mounted on said base portion, said cover comprising an outer surface protective member having a substantially semioval bottom wall, an end wall and a peripheral wall, a gripper having a pair of gripper plates and having an open end, and an engaging part for engagement with an articulator, said gripper being detachably mounted in said outer surface protective member such that said open end faces toward a tip of said outer surface protective member.

13. The working cast arrangement as claimed in claim 12, wherein said engaging part comprises a magnetic member.

14. The working cast arrangement as claimed in claim 12, wherein said outer surface protective member has a through hole so that said gripper mounted in said outer surface protective member can be pushed out of said protective member by pushing through said bole.

15. The working cast arrangement as claimed in claim 12, wherein said gripper has a partitioning plate extending along a central axis of said gripper toward the tip of said outer surface protective member.

16. The working cast arrangement as claimed in claim 12, wherein said cover further comprises a positioning part provided on the outer surface of the bottom wall of said outer surface protective member for holding the cover in position when engaged with an articulator.

17. An articulator comprising a base, a column extending vertically from one end of said base, a support arm pivotally mounted to a tip of said column, a support member provided at a tip of said support arm so that said support member can face said base, each of said base and said support member having on its opposed surface a retainer plate detachably engageable with one of: a cover comprising an outer surface protective member having a substantially semioval bottom wall, an end wall and a peripheral wall, a gripper having a pair of gripper plates and having an open end, and an engaging part for engagement with an articulator, said gripper being detachably mounted in said outer surface protective member such that said open end faces toward a tip of said outer surface protective member; and a base member comprising a substantially semioval plate carrying on its back an engaging part engageable with an articulator and a positioning part for holding the base member in position relative to the articulator.

18. The articulator as claimed in claim 17 further comprising a holder arrangement for selectively holding said respective retainer plate rotatable and pivotable relative to said base and said support member and nonrotatable and nonpivotable relative to said base and said support member.

19. The articulator as claimed in claim 18 wherein said retainer plates are mounted so as to be movable toward and away from said base and said support member, respectively.

20. The articulator as claimed in claim 18 wherein each of said retainer plates has a magnetic member on a front side thereof.

21. The articulator as claimed in claim 10 wherein each of said retainer plates is provided with a positioning part associated with the positioning part of said cover or said base member.

22. The articulator as claimed in claim 17 herein said retainer plates are mounted so as to be movable toward and away from said base and said support member, respectively.

23. The articulator as claimed in claim 22 wherein each of said retainer plates has a magnetic member on a front side thereof.

24. The articulator as claimed in claim 22 wherein each of said retainer plates is provided with a positioning part associated with the positioning part of said cover or said base member.

25. The articulator as claimed in claim 17 wherein each of said retainer plates has a magnetic member on a front side thereof.

26. The articulator as claimed in claim 25 wherein each of said retainer plates is provided with a positioning part associated with the positioning part of said cover or said base member.

27. The articulator as claimed in claim 17 wherein each of said retainer plates is provided with a positioning part associated with the positioning part of said cover or said base member.

28. The articulator claimed in claim 17, wherein said engaging part comprises a magnetic member.

29. The articulator claimed in claim 17, wherein said outer surface protective member has a through hole so that said gripper mounted in said outer surface protective member can be pushed out of said protective member by pushing through said hole.

30. The articulator claimed in claim 17, wherein said gripper has a partitioning plate extending along a central axis of said gripper toward the tip of said outer surface protective member.

31. The articulator claimed in claim 17, wherein said cover further comprises a positioning part provided on the outer surface of the bottom wall of said outer surface protective member for holding the cover in position when engaged with an articulator.

* * * * *